(12) United States Patent
Mallinson et al.

(10) Patent No.: US 10,433,046 B2
(45) Date of Patent: Oct. 1, 2019

(54) DETERMINATION OF ENVIRONMENTAL EFFECTS ON ELECTRICAL LOAD DEVICES

(71) Applicant: ESS Technology, Inc., Milpitas, CA (US)

(72) Inventors: A. Martin Mallinson, Kelowna (CA); Robert Lynn Blair, Pleasanton, CA (US); Christian Leth Petersen, Burnaby (CA); Paul Christopher Scowen, West Kelowna (CA)

(73) Assignee: ESS Technology, Inc., Milpitas, CA (US)

( * ) Notice: Subject to any disclaimer, the term of this patent is extended or adjusted under 35 U.S.C. 154(b) by 0 days.

(21) Appl. No.: 16/130,979

(22) Filed: Sep. 13, 2018

(65) Prior Publication Data

US 2019/0116414 A1    Apr. 18, 2019

Related U.S. Application Data

(60) Provisional application No. 62/558,545, filed on Sep. 14, 2017, provisional application No. 62/567,745, filed on Oct. 3, 2017, provisional application No. 62/568,299, filed on Oct. 4, 2017.

(51) Int. Cl.
*H04R 1/10* (2006.01)
*H03M 1/02* (2006.01)
*H03F 3/45* (2006.01)

(52) U.S. Cl.
CPC ............. *H04R 1/1083* (2013.01); *H03F 3/45* (2013.01); *H03M 1/02* (2013.01); *H04R 2460/01* (2013.01)

(58) Field of Classification Search
CPC ..... H04R 1/1083; H04R 2460/01; H03F 3/45; H03M 1/02
See application file for complete search history.

(56) References Cited

U.S. PATENT DOCUMENTS

2013/0329901 A1* 12/2013 Theiler ................ G10K 11/178
381/71.1
2016/0316297 A1* 10/2016 Yang ...................... H04R 5/033

* cited by examiner

*Primary Examiner* — Andrew L Sniezek
(74) *Attorney, Agent, or Firm* — Gard & Kaslow LLP (57) ABSTRACT

An improved system and method for reducing the ambient noise experienced by a user listening to an earpiece without the use of a microphone is disclosed. An "ambient noise signal" created by the sound pressure wave of the ambient noise acting on the earpiece transducer is obtained. In some embodiments, the ambient noise signal is inverted and fed back, and the inverted signal is added to the intended audio signal being sent to the earpiece so that the ambient noise is cancelled. In other embodiments, a processor receives the ambient noise signal and predicts the modification to the intended audio signal needed to counteract the ambient noise. The ambient noise signal may be obtained by comparing the actual signal across the earpiece transducer to the intended audio signal, or by detecting variations in the current across the transducer from the current generated to drive the transducer.

8 Claims, 5 Drawing Sheets

DETERMINATION OF ENVIRONMENTAL EFFECTS ON ELECTRICAL LOAD DEVICES

This application claims priority to Provisional Application Nos. 62/558,545, filed Sep. 14, 2017, 62/567,745, filed Oct. 3, 2017, and 62/568,299, filed Oct. 4, 2017, each of which is incorporated by reference herein in its entirety.

FIELD OF THE INVENTION

The present invention relates generally to electrical devices and more specifically to the determination and reduction of environmental effects on the operation of electrical load devices.

BACKGROUND OF THE INVENTION

It is often desirable to determine the impact of environmental effects on the operation of electrical devices, and in some cases to counteract such effects. For example, active noise cancellation (ANC) is a desirable feature in earpieces. (As used herein, "earpiece" encompasses any sound reproduction device worn over, on or in a user's ear, including headsets, headphones, or earbuds.) The effect of noise cancellation is to suppress ambient noise without changing an audio signal applied to the earpiece, so that the user is subjected to a lower level of the ambient noise, and the user's listening experience is thus improved. Noise cancellation is particularly useful where the level of ambient noise is substantial, for example in airplanes, trains and other similar environments.

There are three well-known types of ANC. In "feedforward" ANC, a microphone is placed away from the earpiece, and receives the ambient noise before the user does. In "feedback" embodiments of ANC, a microphone is placed near the earpiece, or even in the earpiece itself, and thus receives the ambient noise in substantially the same way as the user does. Those of skill in the art will be aware of the limitations of both feedforward and feedback ANC, and of the use of "hybrid" embodiments of ANC that include both feedforward and feedback techniques in an effort to achieve better noise cancellation.

The present application concerns feedback ANC. In feedback ANC, the microphone near or in the earpiece receives the ambient noise, resulting in an ambient noise signal. A signal that is an inverted copy of the ambient noise signal is added to the intended audio signal such that the addition of the inverted copy in the desired audio program cancels, to some degree, the perceived ambient noise. Thus, additional noise, i.e., the inverted copy, is added to the desired audio program to cancel the ambient noise, and the user perceives that the ambient noise level is lower.

The amplitude and phase of the inverted noise-cancelling signal is preferably selected so as to optimize this perceived reduction of ambient noise. This is typically accomplished by the use of an adaptive feedback loop of some kind; in some embodiments, a Finite Impulse Response Filter (FIR) is configured using a Least Mean Squares (LMS) algorithm to optimally remove the noise. Such techniques are well known in the art.

However, the need for a microphone to detect the ambient noise results in limitations on the ability to successfully perform active noise cancellation. One is that the proximity of the microphone and the earpiece driver is critical to performance; the speed of sound in air means that even small differences in position between the microphone and the earpiece transducer can cause a delay that prevents the noise cancellation loop from cancelling high frequency sounds.

Accordingly, it would be useful to be able to perform active noise cancellation without needing a microphone to detect the ambient noise.

SUMMARY OF THE INVENTION

An improved system and method for determining a signal that is representative of an environmental effect on an electrical load while the electrical load is operating based upon an input signal is disclosed.

One embodiment discloses a circuit for determining a signal that is representative of an environmental effect on an electrical load while the electrical load is operating based upon an input signal, comprising: a first differential amplifier having a first input receiving the input signal and a second input receiving an output of the first differential amplifier, the output of the first differential amplifier driving the electrical load thereby causing the second input to receive a signal representing the input signal and including environmental effect on the electrical load; a second differential amplifier having a first input receiving the input signal and a second input receiving an output of the second differential amplifier, the output of the second differential amplifier driving a load having an impedance equal to an impedance of the electrical load, thereby causing the second input to receive a signal representing the input signal; and a third differential amplifier having a first input receiving the output of the first differential amplifier and a second input receiving the output of the second differential amplifier, thereby producing as an output of the third differential amplifier a signal which is a difference between the input signal and the signal applied to the electrical load by both the input signal and the environmental effect.

Another embodiment discloses a circuit for determining a signal that is representative of, and reducing, an environmental effect on an electrical load while the electrical load is operating based on an input signal, comprising: a current output amplifier configured to output a current and the input signal to the electrical load; a voltage output amplifier configured to detect variations in current in a resistor connected to the electrical load caused by changes in voltage at the electrical load due to the environmental effect on the electrical load; a subcircuit configured to amplify the voltage across the resistor in the voltage output amplifier to generate a signal that is representative of the environmental effect and transmit the representative signal to the processor; and a processor configured to adjust the input signal thereby causing the current output amplifier to alter the current provided to the electrical load to reproduce the input signal while leaving no current flowing through the resistor.

Still another embodiment discloses a method for determining a signal that is representative of an environmental effect on an electrical load while the electrical load is operating based on an input signal, comprising: providing the input signal as a first input to a first differential amplifier, a second input of the first differential amplifier receiving an output of the first differential amplifier, the output of the first differential amplifier driving the electrical load thereby causing the second input to receive a signal representing the input signal and including the environmental effect on the electrical load; providing the input signal as a first input to a second differential amplifier, a second input of the second differential amplifier receiving an output of the second differential amplifier, the output of the second differential amplifier driving a load having an impedance equal to an impedance of the electrical load, thereby causing the second input to receive a signal representing the input signal; and providing to a third differential amplifier as a first input the output of the first differential amplifier and as a second input the output of the second differential amplifier, thereby producing as an output of the third differential amplifier a signal which is a difference between the input signal and the signal applied to the electrical load by both the input signal and the environmental effect.

Yet another embodiment discloses a method for determining a signal that is representative of, and reducing, an effect of an environmental effect on an electrical load while the electrical load is operating based on an input signal, comprising: outputting, from a current output amplifier, a current and the input signal to the electrical load; detecting, by a voltage output amplifier, variations in current in a resistor connected to the electrical load caused by changes in voltage at the electrical load due to the environmental effect on the electrical load; amplifying, by an amplifier circuit, the voltage across the resistor in the voltage output amplifier to generate a signal that is representative of the environmental effect and transmitting the representative signal to the processor; and adjusting, by a processor, the input signal thereby causing the current output amplifier to alter the current provided to the electrical load to reproduce the input signal while leaving no current flowing through the resistor.

DETAILED DESCRIPTION OF THE INVENTION

An improved system and method for determining a signal that is representative of an environmental effect on an electrical load while the electrical load is operating based upon an input signal is disclosed. An example showing how this can be used to reduce the ambient noise experienced by a user listening to an earpiece without the use of a microphone is provided.

In various embodiments, the system and method utilize the fact that an electrical load operating based upon an input signal will often respond in reverse, and produce a signal in response to the impact of some environmental effect. This "reverse signal" can be used to detect a wide variety of conditions, and in many cases can also be used to ameliorate such conditions.

For example, with respect to noise reduction specifically, an electroacoustic transducer for producing a sound pressure wave (hereafter "a sound" or "audio") in response to an electrical audio signal (hereafter an "audio signal") will also operate in reverse and will produce an audio signal in response to receiving a sound, such as ambient noise around a user. The microphone of the prior art located in or near the earpiece is omitted, and the "microphone effect" of an earpiece is used to provide a signal representative of the ambient noise to the adaptive feedback loop that optimizes the noise suppression.

It is well known in the art that any transducer that produces sound in response to an audio signal, such as the transducer in an earpiece or a loudspeaker, does so by moving in response to the audio signal applied to it and thus producing a sound corresponding to the audio signal. The process works in reverse as well; when such a transducer is subjected to an external sound, it in turn produces an electrical signal, although this signal will typically be orders of magnitude smaller than the signal that is used to drive the transducer.

This is the same principle as that of a microphone, which produces an electrical signal in response to sound. The reverse signal produced by a transducer normally used to produce sound in response to an external sound may be thought of as a "back audio signal" or "ambient noise signal" to differentiate it from the audio signal that is normally applied to the transducer to cause it to produce sound.

The described system and method omit a microphone as used in the prior art, and instead take advantage of this "microphone effect" of an earpiece to provide an ambient noise signal representative of the ambient noise to the adaptive loop that optimizes the noise suppression. As discussed below, because the ambient noise signal is much smaller than the audio signal, care must be taken in its detection and amplification to a signal large enough to be inverted and added to the audio signal.

Figures 1A, 1B, 1C:
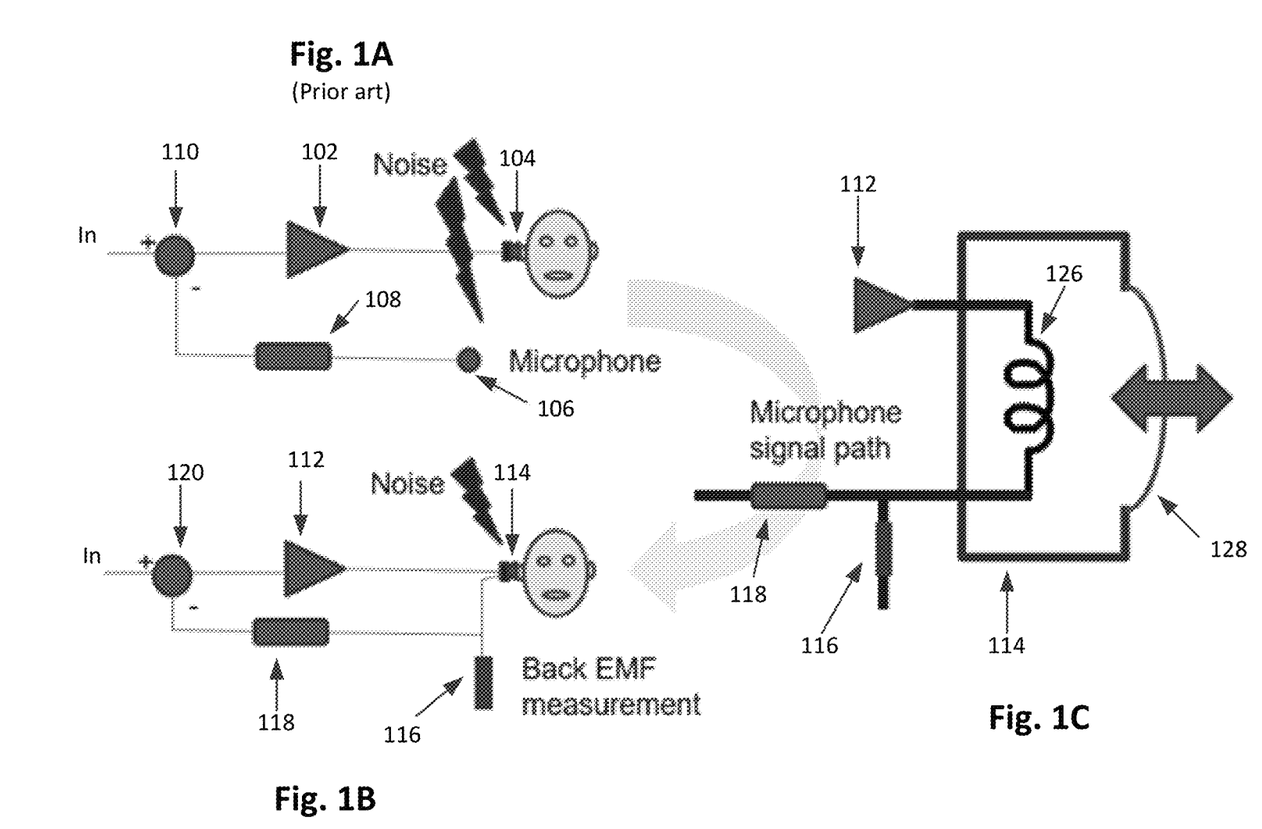
FIG. 1A is a diagrammatic representation of an exemplary prior art system with a microphone for detecting ambient noise that may be used to perform feedback active noise cancellation.
FIG. 1B is a diagrammatic representation of an exemplary system without a microphone for detecting ambient noise that may be used to perform feedback active noise cancellation according to some embodiments.
FIG. 1C is a diagrammatic representation of an earpiece that may be used in the system of FIG. 1B according to some embodiments.

FIG. 1A is a diagrammatic representation of an exemplary prior art system with a microphone for detecting ambient noise that may be used to perform feedback active noise cancellation. An amplifier 102 provides an amplified input audio signal to an earpiece 104; however, the user also hears ambient noise. A microphone 106 receives the ambient noise and provides a signal representative of the ambient noise to a circuit 108, as above typically a FIR filter configured with an LMS algorithm, which generates a signal that is an inverted copy of the ambient noise signal. The inverted copy is then added to the input signal at adder 110, and the now modified input signal 102 is provided to the earpiece 104. The intent is that the inverted copy of the ambient noise will cancel the ambient noise.

However, it is well known that feedback ANC has certain limitations. One limitation is that the proximity of the microphone and the earpiece transducer that creates the sound that is heard by the user, specifically the distance from the microphone to the membrane of the transducer, is critical to performance. The speed of sound in air means that even a 10 millimeter (mm) difference in position between the microphone and the earpiece transducer prevents the ANC loop from cancelling high frequency sounds. Typically, such an arrangement of a separate microphone and transducer results in an upper limit to the noise suppression of about 1 kilohertz (kHz), i.e., frequencies of unwanted ambient noise above 1 kHz are hard to suppress because the difference of even as little as 10 mm between the microphone and the membrane causes enough delay to destabilize the ANC loop over that frequency.

FIG. 1B is a diagrammatic representation of an exemplary system that may be used to perform feedback active noise cancellation according to some embodiments. As in the system of FIG. 1A, in FIG. 1B again an amplifier 112 provides an amplified input audio signal to an earpiece 114.

However, in FIG. 1B there is no microphone 106; rather, the transducer membrane in earpiece 114 now receives the ambient noise while it produces the audio heard by the user. A detection circuit 116 measures the "back audio signal" and, similarly to the microphone 106 of FIG. 1A, provides a signal representative of the ambient noise to a circuit 118, again typically a FIR filter configured with an LMS algorithm, which again generates a signal that is an inverted copy of the ambient noise signal. As with the system of FIG. 1A, the system of FIG. 1B adds the inverted copy to the input signal at adder 120, and the now modified input signal 112 is provided to the earpiece 114.

FIG. 1C is a diagrammatic representation of an earpiece that may be used in the system of FIG. 1B according to some embodiments. As above, the amplifier 112 provides the amplified audio signal to earpiece 114, detection circuit 116 measures the ambient noise signal representing the ambient noise, and circuit 118 generates the inverted copy of the ambient noise signal.

FIG. 1C further illustrates the electromagnetic coil 126 that receives the audio signal from amplifier 112 and moves the transducer membrane 128 of the earpiece. However, membrane 128 also experiences movement due to the ambient noise, and this movement is translated back into an electrical signal by coil 126, which is detected by detection circuit 116 and fed back to circuit 118 as above.

This configuration improves on the prior art by eliminating any delay between the ambient noise arriving at the microphone and at the membrane, since they are the same membrane. Thus, the effectiveness of the noise cancellation, particularly at higher frequencies, is much better. In addition, the system of FIG. 1B allows any unmodified earpiece to be used with ANC, and thus avoids the additional cost of a microphone.

An ambient noise signal may be detected by subtracting the intended audio signal that is to drive the transducer from the signal that the transducer actually receives. Since the actual transducer signal contains the ambient noise signal, removing the outgoing audio signal leaves only the ambient noise signal.

Figure 2:
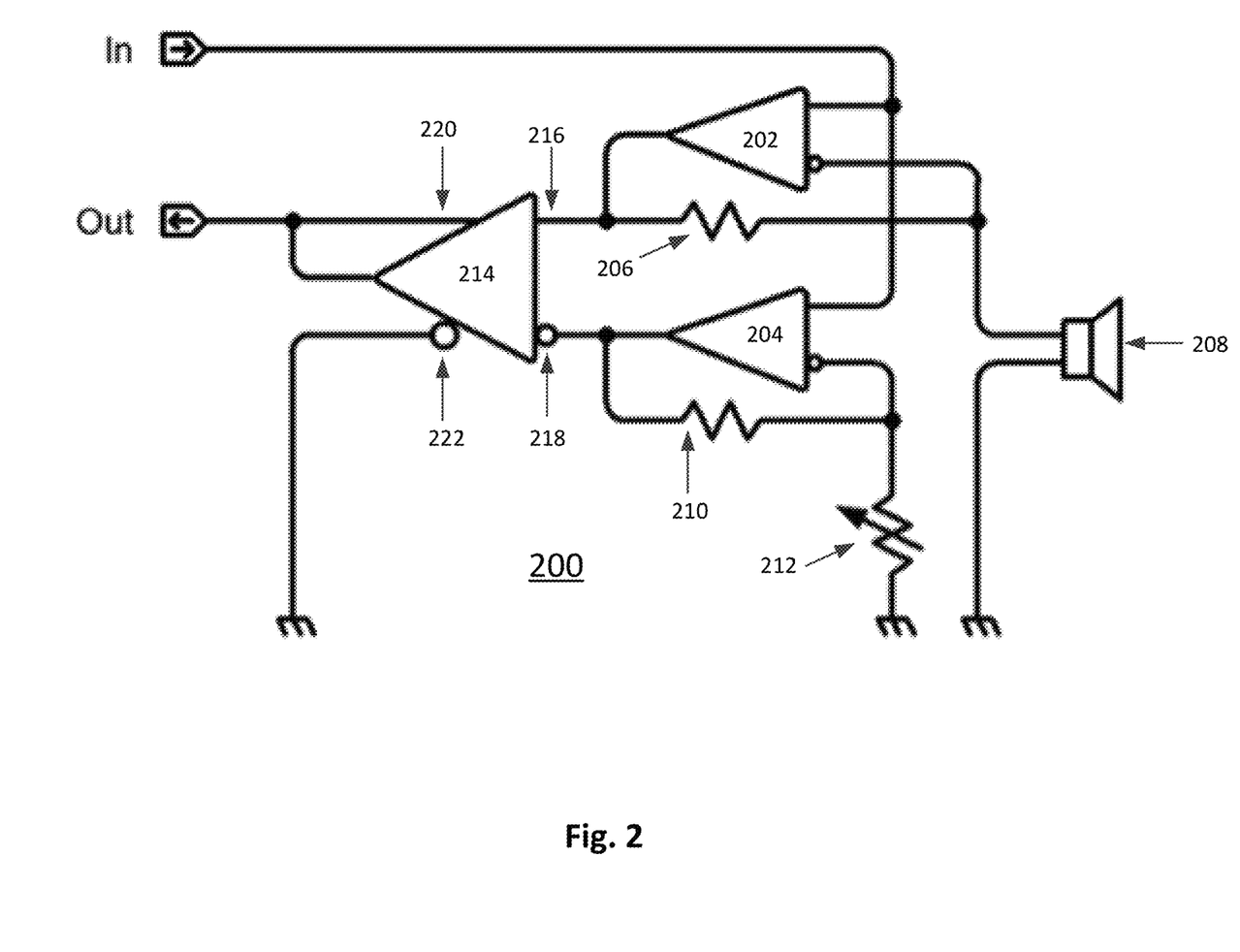
FIG. 2 illustrates a feedback active noise cancellation circuit without a microphone for detecting ambient noise according to some embodiments.

One approach for such subtraction is to create a replica of the transducer load, subtract the current through the replica from the actual load current, and treat the residual load current as the ambient noise signal. FIG. 2 illustrates a feedback active noise cancellation circuit 200 using this principle according to some embodiments.

An input audio signal is applied to the non-inverting inputs of two differential operational amplifiers ("op-amps," called "amplifiers" herein) 202 and 204. Amplifier 202 has a feedback loop through resistor 206, through which the output of amplifier 202 is applied to earpiece 208 and back to the inverting input of amplifier 202. As will be apparent to those of skill in the art, this will result in amplifier 202 driving resistor 206 to cause both inputs of amplifier 202 to see the same signal, and earpiece 208 will thus see the same signal. One of skill in the art will appreciate that the input audio signal will typically come from a digital-to-analog converter (DAC), which converts a digital audio signal into an analog signal, and the output will typically be passed to an analog-to-digital converter (ADC) that does the reverse; however, the described circuit may also be used with an entirely analog system.

Amplifier 204 similarly has a feedback loop through resistor 210, which has the same value as resistor 206, to the inverting input of amplifier 204 and to ground through resistor 212, which may be an adjustable resistor. Resistor 212 is selected or adjusted to have the same impedance as earpiece 208, and thus the voltages on the inverting inputs of amplifiers 202 and 204 will be the same in the absence of ambient noise. The current required to drive the earpiece flows through resistor 206, and an equal current flows through resistor 210 because the impedance of resistor 212 is equal to that of earpiece 208.

Amplifier 214 is not an ordinary operational amplifier, but an instrumentation amplifier ("in-amp") that amplifies the difference between two input signal voltages while rejecting any signals that are common to both inputs and thus can typically measure small signals in noisy environments; one example of such an instrumentation amplifier is an AD524 amplifier from Analog Devices.

As is known in the art, while ordinary amplifiers have two inputs, i.e., non-inverting and inverting, an instrumentation amplifier has four inputs. Two of these inputs are like the inputs on a normal amplifier, and are inputs 216 and 218 to amplifier 214 in FIG. 2. The other two inputs 220 and 222 to amplifier 214 provide a differential feedback path that can be configured, with various gains, to balance the differential signal from the input terminals 216 and 218. The output of amplifier 214 is fed back to its non-inverting feedback input 220, while the inverting feedback input 222 is connected to ground. The output of amplifier 214 in this configuration will be the difference between the two inputs 216 and 218 to amplifier 214 times the gain of amplifier 214.

Since amplifier 214 receives at its inputs 216 and 218 the outputs of amplifiers 202 and 204, when those outputs are the same in the absence of ambient noise, the output of amplifier 214 will be zero. However, when there is ambient noise, the pressure from the ambient noise sound wave on the earpiece transducer causes the current through resistor 206 to change, while the current through the matching impedance of resistor 212 does not change. The outputs of amplifiers 202 and 204, which are the same when only the audio signal is present, are different when there is ambient noise. This difference is the ambient noise signal that may then be amplified by amplifier 214 and sent to a conventional circuit such as circuit 118 of FIG. 1B, which again may be a FIR filter using an LMS algorithm, for inverting.

The use of an instrumentation amplifier as amplifier 214 rather than a conventional amplifier is desirable because, as above, the ambient noise signal is very small, much smaller than the audio signal used to drive the earpiece transducer. For example, a typical earbud having an impedance of 6 to 600 ohms may be driven by a signal as large as 500 millivolts (mV), but generate only 5 to 50 microvolts (μV) of reverse audio signal when acting as a microphone. Thus, the ratio of the driving audio signal to the reverse audio signal to be detected may be as much as 100,000 to 1 (500 mV to 5 μV).

It may appear that this ratio is so large that the ambient noise signal cannot be present, or cannot be detected, while the transducer is momentarily displaced when audio is playing in the earpiece. This is found not to be the case, as experiments show that the ambient noise signal created by the ambient sound reaching the transducer is always present as a small signal superimposed on the audio signal being used to drive the transducer, and can be separated from the audio signal. The large gain of an instrumentation amplifier is desirable to increase the voltage of the reverse audio signal to a substantial output from amplifier 214 to be further processed according to the prior art as described above.

However, even presently available instrumentation amplifiers do not provide as large a gain as would be optimal given the large difference between the audio signals typically used to drive transducers and the ambient noise signals that can be provided by those transducers. Accordingly, another approach to determining the ambient noise signal may be more easily implemented.

The other approach to determining the ambient noise signal is to try to measure the actual ambient noise signal and estimate what the audio signal should be to drive the ambient noise signal to zero. As this is possible without amplifying and inverting the ambient noise signal, the high gain of an instrumentation amplifier is not needed.

Figure 3:
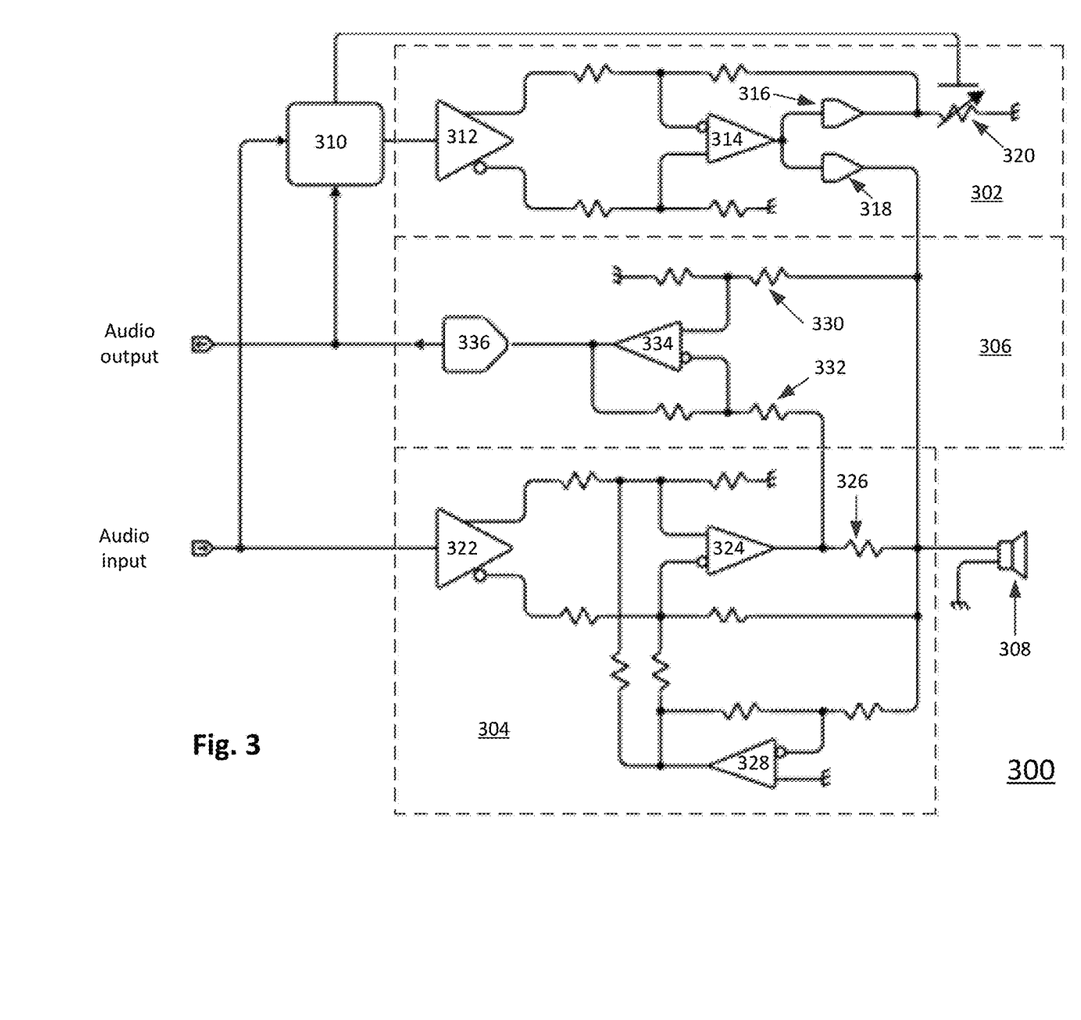
FIG. 3 illustrates a feedback active noise cancellation circuit without a microphone for detecting ambient noise according to other embodiments.

FIG. 3 illustrates a feedback active noise cancellation circuit 300 according to some embodiments using this principle. Circuit 300 comprises three subcircuits 302, 304 and 306. Subcircuit 302 provides the current to drive the earpiece 308; subcircuit 304 receives the ambient noise signal; and subcircuit 306 amplifies the ambient noise signal and converts it back into a digital signal to be fed to processor 310.

Subcircuit 302 is a current output amplifier driving the earpiece 308. It functions largely as a conventional amplifier, except that the output stage is replicated. An audio signal is input to processor 310 and processed as will be explained further below, and the output of processor 310 is input to a DAC 312. DAC 312 turns a digital audio signal into an analog audio signal suitable for driving a transducer, and the analog audio signal is input to an amplifier 314, which in turn drives two output stages 316 and 318.

Output stage 316 drives a variable load resistor 320 as discussed further below, while output stage 318 drives the earpiece 308. When operating as explained, output stage 318 provides all of the current needed to properly drive the transducer in earpiece 308.

In the illustrated embodiment, output stages 316 and 318 operate in the same way except that output stage 318 provides 20 times the current of output stage 316. In some cases, output stage 318 may comprise 20 instances of the circuit of output stage 316. As is apparent from FIG. 3, both output stage 316 and output stage 318 must also receive the same output voltage from amplifier 314.

Those of skill in the art will appreciate that it is desirable to keep DAC 312 operating within its "sweet spot," i.e., the linear portion of its range. Many semiconductor devices, and thus standard DACS, typically have a supply voltage of 3.3 volts. As will be appreciated by those of skill in the art, an operating voltage of 1 volt is thus often considered to be within the linear portion of the range of a DAC. Under the control of processor 310, variable resistor 320 operates as a control mechanism to accomplish this.

In the illustrated embodiment, variable resistor 320 has an impedance that is 20 times the impedance of earpiece 308. As will be seen, this corresponds to the current output of output stage 318 being 20 times that of output stage 316.

Suppose earpiece 308 has an impedance of 60 ohms. At the desired voltage of 1 volt, the current flowing through earpiece 308, which is provided through output stage 318, will be slightly over 16 milliamps. Because output stage 316 receives 1/20 of the current that output stage 318 receives, 800 milliamps will flow through output stage 316.

Variable resistor 320 has an impedance 20 times greater than that of earpiece 308, i.e., 1200 ohms. Because this impedance of variable resistor 320 is significantly lower than the feedback resistor, the 800 milliamps from output stage 316 will mostly flow through variable resistor 320. The 800 milliamps across the 1200 ohms of variable resistor 320 results in the same expected voltage from DAC 312 of 1 volt.

Next, suppose earpiece 308 is replaced with a new earpiece having an impedance of 6 ohms. Now the current through earpiece 308 at 1 volt, which also passes through output stage 318, will be 160 milliamps. The current through output stage 316, which again is 1/20 of the current through output stage 318, will be 8 milliamps.

However, when the 8 milliamps passes through the 1200 ohm impedance of variable resistor 320, it will now expect a voltage from DAC 312 of 10 volts, well above the operating voltage of the system of 3.3 volts. Processor 310 can recognize that this is not possible and that even pushing DAC 312 to its upper voltage limit of 3.3 volts will take DAC 312 out of its linear operating range, and can change variable resistor 320 to 120 ohms, so that the 8 milliamps of current across variable resistor 320 again expects a voltage from DAC 312 of 1 volt.

In this way the current-mode DAC 312 is kept in its linear operating range for all of the different expected loads of earpiece 308.

Subcircuit 304 is a voltage output amplifier that also drives earpiece 308. A DAC 322 receives the audio signal, and in turn drives amplifier 324, which is in a conventional differential-to-single ended configuration. Resistor 326 receives the output of amplifier 324, so that any load current required from amplifier 324 must flow through resistor 326. The feedback point of amplifier 324 is such that the output voltage on the node connecting resistor 326 and earpiece 308 must equal the signal from voltage mode DAC 322.

In this embodiment, resistor 326 has an impedance of 300 ohms, significantly higher than the impedance of earpiece 308. However, no current is expected to flow through resistor 326 into earpiece 308 because, as explained below, the action of circuit 300 causes all load current required by the earpiece to flow from subcircuit 302. The only current flowing though resistor 326 is that from the ambient noise signal and this allows the impedance of resistor 326 to be substantially higher than impedance of earpiece 308.

The differential amplifier configuration around amplifier 324 operates to ensure that the voltage at the earpiece is exactly that determined by DAC 322. Subcircuit 306 measures the current that amplifier 324 is providing in order to achieve this output voltage; this allows processor 310 to adjust subcircuit 302 to provide the current to achieve the output voltage instead of it flowing from amplifier 324. In operation, subcircuit 306, processor 310, and subcircuit 302 cooperate to suppress all current flowing out of amplifier 324 through resistor 326. Thus, the voltage across resistor 326 is nominally zero.

The suppression of the voltage across resistor 326 is possible because processor 310 is provided with the audio input signal, the same audio input signal that is applied to DAC 322. Processor 310 adapts, via an LMS or similar algorithm, the current provided from subcircuit 302 until the average value of the voltage across resistor 326 is zero. Consequently, after the LMS algorithm has converged, the audio signal flowing through the processor and into subcircuit 302 is providing an estimate of all the current needed by the earpiece load.

No current from differentially configured amplifier 324 is required to drive the audio content to earpiece 308; rather, all the current to drive earpiece 308 is provided by the predicted current coming from subcircuit 302. Amplifier 324 provides only the difference between the predicted current and the actual current required by the earpiece. If the predicted current were precisely correct, no current would flow through resistor 326.

However, ambient noise that earpiece 308 is picking up from the environment cannot be predicted by processor 310 and is therefore not present in the current output from subcircuit 302. Any ambient noise current must therefore flow through resistor 326.

Amplifier 328 and the resistors associated with it are a circuit that reduces distortion, as further described in U.S. Pat. No. 9,595,931, commonly owned by the assignee of the present application. This portion of subcircuit 304 may optionally be omitted, but without it subcircuit 304 will not function as well as may be desirable.

Subcircuit 306 receives the voltage from resistor 326 through resistor 332, and the voltage of the driving current from output stage 318 through resistor 330. Amplifier 334 amplifies any difference between these two voltages, and passes the amplified result to ADC 336. It will be apparent that if there is no ambient noise, no current will flow through resistor 326, these two voltages will thus be the same, and the outputs of both amplifier 334 and ADC 336 will be zero.

If there is ambient noise, there will be current through, and voltage across, resistor 326, and the output of amplifier 334 will be non-zero. The output of amplifier 334, and thus the output of ADC 336, represents the ambient noise in this case.

The output of ADC 336 allows processor 310 to suppress that part of the digital output from ADC 336 that is due to the audio content. The processor does this via a known LMS algorithm or similar. Processor 310 finds the correlation between the audio content and the digital output of ADC 336 and minimizes the audio content present in the output of ADC 336 by driving the predicted current out of subcircuit 302 and so removing current from resistor 326.

Thus, the output of ADC 336, after the processor has converged, represents only the ambient audio signal, i.e., that part of the microphone action of the earpiece not due to the audio content. The microphone signal alone, which is the ambient noise signal, is present on the output of ADC 336.

In this embodiment, processor 310 is a digital signal processor (DSP). When it receives an ambient noise signal from ADC 326, processor 310 uses the ambient noise signal to cause subcircuit 302 to output a current from amplifier 318 that optimally meets the current required to reproduce the audio signal in earpiece 308, leaving no current through resistor 326 and thus no signal related to the audio content from ADC 326.

Figure 4:
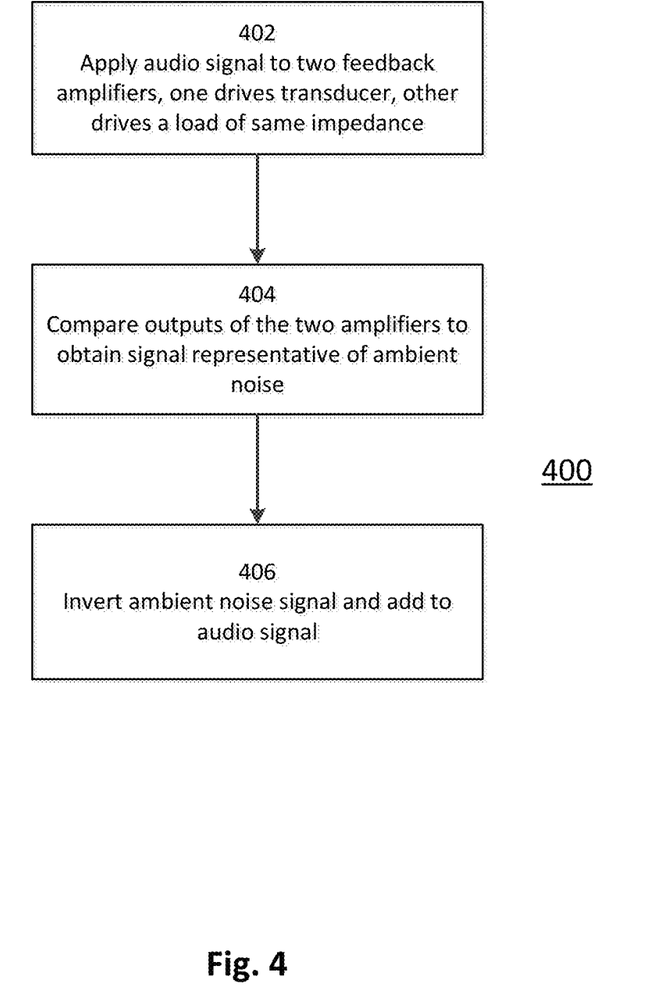
FIG. 4 illustrates a method of feedback active noise cancellation according to some embodiments.

The feedback ANC described herein may be described as a method. FIG. 4 illustrates one method 400 of such feedback ANC according to some embodiments. In step 402, as described above with respect to circuit 200 of FIG. 2, an audio signal is applied to an input of each of two differential amplifiers; each amplifier has a feedback loop of its output to its other input. The output of the first amplifier drives the electroacoustic transducer, and the feedback to the first amplifiers input thus includes any variations in voltage due to the effect of ambient noise on the electroacoustic transducer. The output of the second amplifier drives a load having the same impedance as the electroacoustic transducer, and thus is not subject to such effects of ambient noise.

At step 404 the outputs of the two amplifiers are compared using a third differential amplifier (preferable an instrumentation amplifier as above) and amplified. As above, the outputs of the first and second amplifiers each contain the audio signal, but the output of the first amplifier also contains variations in the voltage of the electroacoustic transducer that represent the effect of ambient noise on the electroacoustic transducer. The difference between the outputs of the first and second amplifiers is thus a signal representative of the ambient noise.

At step 406, as in the prior art, the signal representative of the ambient noise is then inverted, and the inverted signal is added to the audio signal. The inverted signal cancels, or at least significantly reduces, the effect of the ambient noise on the electroacoustic transducer, and thus how much noise the user hears.

Figure 5:
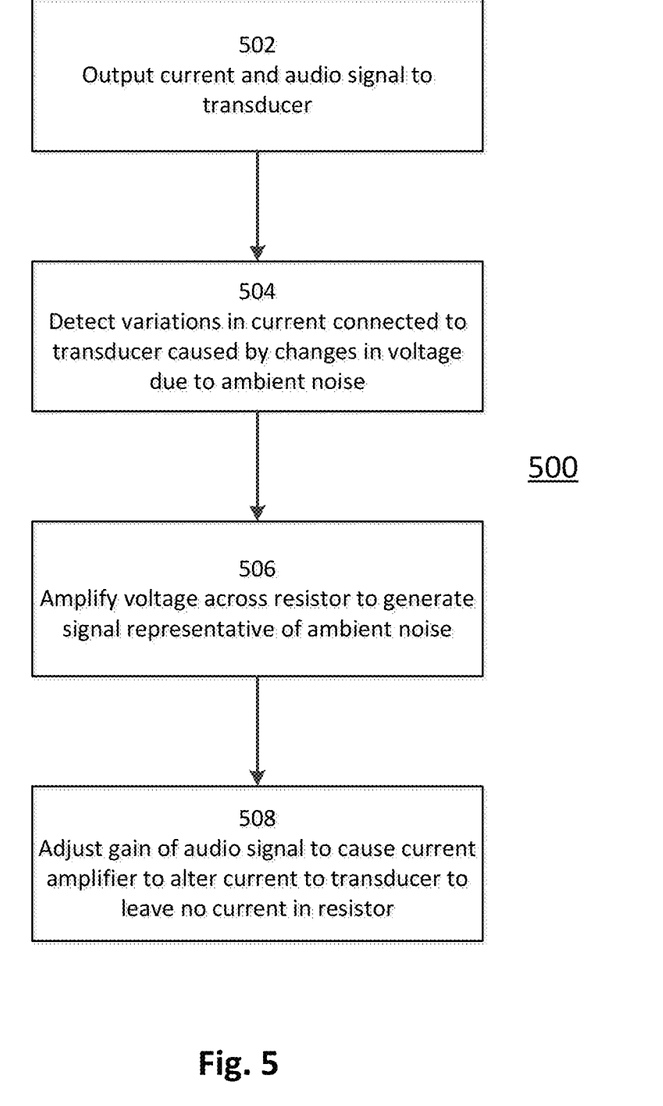
FIG. 5 illustrates another method of feedback active noise cancellation according to some embodiments.

FIG. 5 illustrates another method 500 of feedback ANC according to some embodiments. At step 502, a current and the audio signal are output from a current output amplifier, such as subcircuit 302 of FIG. 3, to the electroacoustic transducer.

At step 504, a voltage output amplifier, such as subcircuit 304 in FIG. 3, detects variations in the current flowing in a resistor connected to the electroacoustic transducer caused by changes in voltage at the electroacoustic transducer due to the effect of ambient noise on the electroacoustic transducer.

At step 506, an amplifier circuit, such as subcircuit 306 in FIG. 3, amplifies the voltage across the resistor in the voltage amplifier to generate a signal that is representative of the ambient noise and transmits it to a processor.

Finally, at step 508, the gain of the audio signal is adjusted by the processor to cause the current output amplifier to alter the current provided to the electroacoustic transducer to reproduce the audio signal while leaving no current flowing through the resistor.

Those of skill in the art will understand how the components described above with respect to FIGS. 2 and 3 are configured to perform the methods of FIGS. 4 and 5, respectively.

One of skill in the art will appreciate that while the present application describes an example of noise reduction in an electroacoustic transducer, the described circuit and method may be used to detect variations in the voltage on any electrical load (for example, any type of electrical component, transducer, motor, etc.) due to any external or environmental factor (for example, pressure, temperature, humidity, the application of a physical force, aging of components, etc.). Further, an advantage of the described circuit and method is that very small variations in the voltage on the electroacoustic transducer due to ambient noise can be detected, even where the audio signal is 100,000 times greater than the ambient noise signal as above. Prior art circuits and methods are not able to achieve this level of precision.

The disclosed system and method has been explained above with reference to several embodiments. Other embodiments will be apparent to those skilled in the art in light of this disclosure. Certain aspects of the described method and apparatus may readily be implemented using configurations or steps other than those described in the embodiments above, or in conjunction with elements other than or in addition to those described above. It will also be apparent that in some instances the order of the processes described herein may be altered without changing the overall result of the performance of all of the described processes, as well as the possible use of different types of air scrubbing systems.

For example, one of skill in the art will appreciate that, like the prior art feedback ANC discussed herein, the feedback ANC of the present application can be used with feedforward ANC to achieve hybrid ANC. It will also be appreciated that there are a variety of algorithms will produce the least mean square (LMS) of a signal. Some such algorithms will converge faster than others, while other such algorithms will be less sensitive to residual error. One of skill in the art will be able to select an appropriate LMS algorithm for a particular application.

In addition, while the present application discusses a method and apparatus for performing ANC with an earpiece transducer, it will be apparent to one of skill in the art that any device that converts an electrical signal to a sound pressure wave can operate in the reverse, i.e., to convert a sound pressure wave to an electrical signal, and thus that the described method and apparatus may also be applied to any type of loudspeaker, whether free-standing or in-wall. It is also expected that with sufficient digital signal processing it will be possible to determine the relative position and movement of objects in the sound field of such loudspeakers, raising many possibilities for applications within the developing "smart home" field.

Still further, while the present application discusses audio signals, it will also be apparent to those of skill in the art that any modulation of sound pressure that is distinct from the expected content of an audio signal can be determined; for example, various types of biometric signals may be recoverable using the method and apparatus described herein.

It will also be appreciated by those skilled in the art that the described circuits and method function by developing a model of the load (the earpiece herein) when that load is responsive to the driven signal alone. The correlation between the load and the driven signal is found and used to predict the load current. The error in the prediction represents useful information. While the example herein is microphone action of an electroacoustic transducer, as above, this is by no means the only possibility: for example, a motor may be the electrical load driven by the described circuit, and the load current prediction will provide the constant force output current. Any variation in the mechanical load will be evident in the deviation of the prediction from the actual load current. For example, a mechanical finger, driven by a motor, will exhibit a significant deviation from the predicted current when the fingers touch. While the prior art discloses some techniques for detecting such variations, the ratio of variation to input signal is limited to about 100 to 1, while as above the circuit and method disclosed herein can detect variations where the ratio to the input signal is 100,000 to 1.

In addition, circuit 300 herein includes processor 310, which has a frequency dependence, a necessary feature of the LMS algorithm used in a FIR filter in the prior art; it will be evident to those skilled in the art that the state variables of the converged algorithm represent the frequency dependence of the load current. Variability of the load, including its frequency dependence, may also be used to determine degradation with age, variation of ambient temperature, etc.

It should also be appreciated that the described method and apparatus can be implemented in numerous ways, including as a process, an apparatus, or a system. The methods described herein may be implemented by program instructions for instructing a processor to perform such methods, and such instructions recorded on a computer readable storage medium such as a hard disk drive, floppy disk, optical disc such as a compact disc (CD) or digital versatile disc (DVD), flash memory, etc. It may be possible to incorporate some methods into hard-wired logic if desired. It should be noted that the order of the steps of the methods described herein may be altered and still be within the scope of the disclosure.

It is to be understood that the examples given are for illustrative purposes only and may be extended to other implementations and embodiments with different conventions and techniques. While a number of embodiments are described, there is no intent to limit the disclosure to the embodiment(s) disclosed herein. On the contrary, the intent is to cover all alternatives, modifications, and equivalents apparent to those familiar with the art.

In the foregoing specification, the invention is described with reference to specific embodiments thereof, but those skilled in the art will recognize that the invention is not limited thereto. Various features and aspects of the above-described invention may be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A circuit for determining a signal that is representative of an environmental effect on an electrical load while the electrical load is operating based upon an input signal, comprising:
   a first differential amplifier having a first input receiving the input signal and a second input receiving an output of the first differential amplifier, the output of the first differential amplifier driving the electrical load thereby causing the second input to receive a signal representing the input signal and including the environmental effect on the electrical load;
   a second differential amplifier having a first input receiving the input signal and a second input receiving an output of the second differential amplifier, the output of the second differential amplifier driving a load having an impedance equal to an impedance of the electrical load, thereby causing the second input to receive a signal representing the input signal; and
   a third differential amplifier having a first input receiving the output of the first differential amplifier and a second input receiving the output of the second differential amplifier, thereby producing as an output of the third differential amplifier a signal which is a difference between the input signal and the signal applied to the electrical load by both the input signal and the environmental effect.

2. The circuit of claim 1 wherein the third differential amplifier is an instrumentation amplifier.

3. The circuit of claim 2 wherein the instrumentation amplifier has a third input that receives the output of the instrumentation amplifier and a fourth input that is connected to a ground.

4. The circuit of claim 1 wherein the input signal is an audio signal, the electrical load is an electroacoustic transducer, and the environmental effect is ambient noise acting on the electroacoustic transducer.

5. A method for determining a signal that is representative of an environmental effect on an electrical load while the electrical load is operating based on an input signal, comprising:
   providing the input signal as a first input to a first differential amplifier, a second input of the first differential amplifier receiving an output of the first differential amplifier, the output of the first differential amplifier driving the electrical load thereby causing the second input to receive a signal representing the input signal and including the environmental effect on the electrical load;

providing the input signal as a first input to a second differential amplifier, a second input of the second differential amplifier receiving an output of the second differential amplifier, the output of the second differential amplifier driving a load having an impedance equal to an impedance of the electrical load, thereby causing the second input to receive a signal representing the input signal; and providing to a third differential amplifier as a first input the output of the first differential amplifier and as a second input the output of the second differential amplifier, thereby producing as an output of the third differential amplifier a signal which is a difference between the input signal and the signal applied to the electrical load by both the input signal and the environmental effect.

6. The method of claim 5 wherein the third differential amplifier is an instrumentation amplifier.

7. The method of claim 6 further comprising providing the output of the instrumentation amplifier as a third input to the instrumentation amplifier and a connecting a fourth input of the instrumentation amplifier to a ground.

8. The method of claim 5 wherein the input signal is an audio signal, the electrical load is an electroacoustic transducer, and the environmental effect is ambient noise acting on the electroacoustic transducer.

* * * * *